United States Patent [19]

Rügheimer

[11] Patent Number: 4,557,261
[45] Date of Patent: Dec. 10, 1985

[54] CONNECTION SYSTEM FOR FLUID LINES HAVING TELESCOPING CONNECTING ELEMENTS, IN PARTICULAR FOR RESPIRATORS OR ANESTHETIC UNITS

[76] Inventor: Erich Rügheimer, Maximilianplatz 1, D-8520 Erlangen, Fed. Rep. of Germany

[21] Appl. No.: 328,694

[22] Filed: Dec. 8, 1981

[30] Foreign Application Priority Data

Dec. 20, 1980 [DE] Fed. Rep. of Germany ....... 3048223

[51] Int. Cl.$^4$ .............................................. A62B 9/04
[52] U.S. Cl. .............................. 128/202.27; 128/912; 604/283; 604/284; 785/155; 785/276; 785/317; 785/320; 285/110; 285/DIG. 22; 403/325; 403/329
[58] Field of Search ............... 285/155, 276, 317, 320, 285/DIG. 22, 110, 347, 319, 7, 318; 403/325, 326, 329, 330; 128/202.27, 912, 204.26; 604/283, 284, 326; 251/149.9; 267/158, 160, 163

[56] References Cited

U.S. PATENT DOCUMENTS

| 593,196 | 11/1897 | Bernhardt | 285/317 |
| 793,103 | 6/1905 | Scholtz | 285/317 |
| 796,220 | 8/1905 | Jones | 285/317 |
| 1,096,696 | 5/1914 | Derbyshire | 285/317 |
| 3,245,698 | 4/1966 | Fromknecht | 285/319 |
| 3,552,778 | 1/1971 | Muller | 285/276 |
| 4,039,213 | 8/1977 | Walters | 285/317 |
| 4,220,360 | 9/1980 | Jacek et al. | 285/317 |

OTHER PUBLICATIONS

Muchler, H. Chr.: Das Technische Narkoserisiko Prakt. Anasth., 13 (1979), 368–378.
Craig, J., Wilson M. E.: A Survey of Anasthetic Misadventures, Anasthesia, 36 (1981), 933–936.
Cooper, Jeffrey B., An Analysis of Major Errors, Anesthesiology, 60 (1984) 34–42.
Cooper, J. B., et al.: Preventable Anasthesia Mishaps, Anesthesiology, 49 (1978), 399–406.
Utting, J. E. et al.: Human Misadventure in Anasthesia, Candad, Anasth. Soc. J., 26 (1979), 472–478.
Rendell Baker, L.: Problems with Anasthetic and Respiratory Therapy Equip. Lat. Anesth. Clin., vol. 20, 1982, No. 3, S53–71 and 83–85.
Orkin, F. K., Cooperman L. H.: Complications in Anesthesiology, Philadelphia, Toronto, 1983, S. 165–172.

Primary Examiner—Henry J. Recla
Assistant Examiner—Karin M. Reichle
Attorney, Agent, or Firm—Browdy and Neimark

[57] ABSTRACT

A connection system for respirator or anesthesia units with a Y-piece including an inhalation hose socket, an exhalation hose socket and a connector attachment piece as well as a tubular connector, connectable with the connector attachment piece, having a tube attachment for an endotracheal tube at one end, and at its opposite end a continuous annular groove in its exterior circumference, the connector attachment piece including a spring biased fastening member provided transversely to the longitudinal axis of the connector attachment piece for elastically engaging the annular groove under spring action. The connection system further includes a hand-operable unfastening mechanism for overriding the spring action of the fastening member, and the fastening member includes a lever having inner and outer arms, a pivot and a spring-loading member for the outer arm. The connector attachment piece includes a slot extending through its sidewall to receive the lever which is positioned in the slot so that at least a portion of the inner lever arm extends into the lumen of the connector attachment piece. The pivot extends through the slot with the lever being parallel to the longitudinal axis of the connector attachment piece. A spring element interposed between the connector attachment piece and the outer arm biases the lever inner arm into engagement with the annular groove.

11 Claims, 18 Drawing Figures

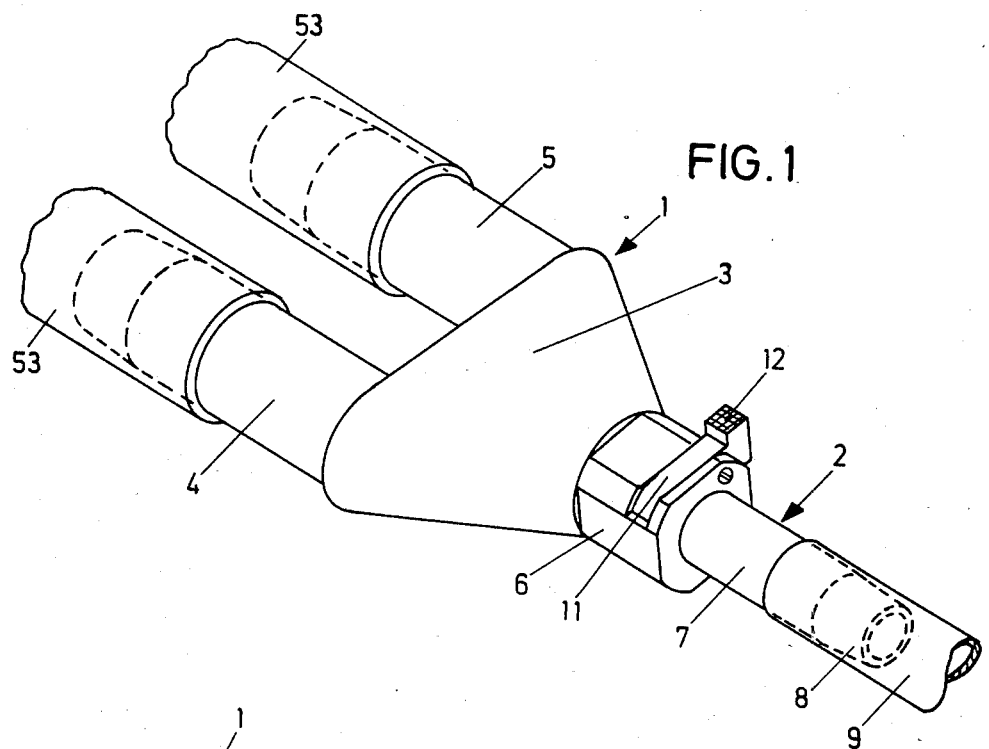
FIG.1
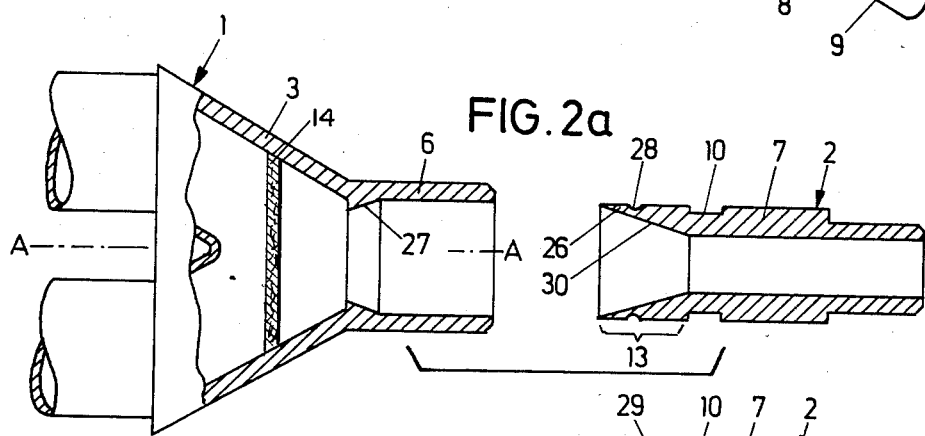
FIG.2a
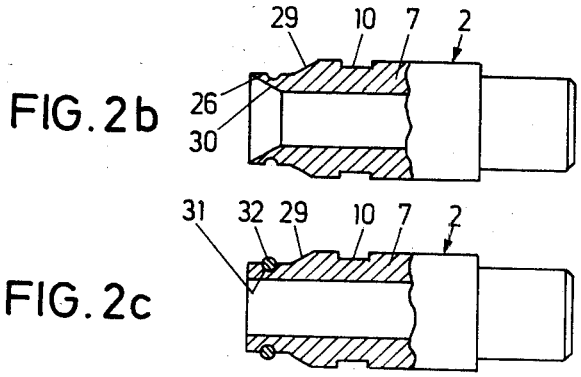
FIG.2b
FIG.2c

CONNECTION SYSTEM FOR FLUID LINES HAVING TELESCOPING CONNECTING ELEMENTS, IN PARTICULAR FOR RESPIRATORS OR ANESTHETIC UNITS

FIELD OF THE INVENTION

The invention relates to a connection system for fluid lines having connecting elements which can be fitted into one another in telescoping fashion, in particular for respirators or anesthetic units. The system has a Y throat piece telescoping with an inhalation hose connector end, an exhalation hose connector end and a connector attachment piece. The system also includes a connector and a tube attachment for an endotracheal tube which can be connected with the connector attachment piece.

BACKGROUND OF THE INVENTION

Connection systems of this kind are used in artificially respirating patients with the aid of intubation; for instance, they are used in anesthetic employing an anesthetic unit before and during an operation; they are also used for long-term patient respiration, for instance in intensive-care units. A respirator or anesthetic unit is attached to a Y piece via inhalation and exhalation lines in the form of rubber or plastic tubes, the tubes or hoses being pushed onto an inhalation or exhalation hose connector end (the legs of the Y piece). The Y piece attaches to a connector attachment piece into which a connector having a tube attachment can be inserted. An endotracheal tube which is passed into the airway of the patient is then telescoped onto the tube attachment of the connector.

It is important that the connection between the Y piece and the connector can be released very quickly in a simple manner and with one hand. During normal operation the connection should be capable of rotational movement without detachment such that the connector remains rotatable inside the connector attachment piece. This plug connection is achieved in known connection systems by means of a conical shaped embodiment of the terminal section of the connector and an interior opening in the connector attachment piece resulting in a finely-machined seat.

However, in such plug connections there is a danger of an unintended and unnoticed disconnection. If a disconnection is not noticed, or is not noticed quickly enough, there may be a lethal outcome if the patient is incorrectly or no longer respirated.

SUMMARY OF THE INVENTION

It is accordingly the principal object of the invention to achieve a connection system of the type discussed above, which is particularly used between an intubated patient and a respirator or anesthetic apparatus such that loose seals are avoided and unintended disconnections are reliably precluded, yet intended and required disconnection can be quickly effected simply and with one hand. There must be no narrowing of the flow path of the air needed for breathing ($O_2$) or of the anesthetic gas being used (e.g., $N_2O$) as a consequence of securely fastening the connections. The connection system should also be sterilizable in a simple manner, but individual connecting elements may also be employed for one-time use, so that it is possible to eliminate some disinfection procedures which are associated with high cost and unreliability.

This object is attained in accordance with the invention, in a connection system of the general type discussed above, substantially by providing the following structures: An annular groove is provided passing all around the wall of a connecting element, and at least one fastening element is also provided, which is disposed on the other connecting element and elastically engages the annular groove subject to the action of a spring located therein. The connecting elements are structured to be freely rotatable relative to one another, and at least one selectively actuatable unfastening element intermittently overrides the spring action of the fastening element. A sealing means disposed at one end area of the insertable connecting element and cooperating with the inner wall of the other connecting element are also provided.

Thus, the first connecting element is automatically locked to the second connecting element solely by being axially inserted into it; at the same time, the required seal between the two connecting elements is established, so that interruptions in pressure and quantity of the fluid passing through these elements are not permitted to occur. Intended unfastening or disconnection can be effected by the temporary removal of the fastening element from the annular groove by overriding the closing spring force.

In accordance with a preferred exemplary embodiment of the invention, one connecting element is the connector attachment piece connected to a Y piece, the opposite end of the attachment piece telescopically receiving a connector and tube attachment. An annular groove is provided in the outer wall of the connector and the at least one fastening element is provided on the connector attachment piece, transverse to the longitudinal axis thereof, Further, the elastic fastening element is structured as a two-armed lever, spring-loaded at one side and rotatable about a tongue. A spring element, which engages the connector attachment piece at one end and the outer lever arm at the other end, prestresses the fastening element in the locking position.

In an advantageous realization of the exemplary embodiment, a spiral helical spring serves as the spring element; it is disposed in an inner bore in the outer lever arm of the fastening element and an inner bore in the connector attachment piece.

In accordance with a modified exemplary embodiment of the fastening element, the outer lever arm of the fastening element is slotted and has a yielding rib which is supported on the connector attachment piece when it is in the locked condition. The required resilient pressure is attained by means of the yielding elasticity of this rib.

It is particularly advantageous if the outer lever arm and/or the connector attachment piece has an oblique face, which permits the unlocking process to occur and provides a terminal limitation for the unlocking stroke of the outer lever arm of the fastening element.

To attain the required sealing effect, it is advantageous to provide, in a further embodiment of the invention, that the forward end of the connector, that is, the end which is insertable into the connector attachment piece, is shaped to taper in conical fashion and to merge into a sealing lip, which rests in an elastically yielding manner against an analogously shaped wall section of the inner wall of the connector attachment piece. The required contacting force is provided by the locking action effected between the annular groove and the fastening element of the two connecting elements.

In order to make this contact pressure of one sealing lip against the analogously shaped wall section of the inner wall of the connector attachment piece more easily attainable, it is advantageous if an outer annular groove is provided in the area where the connector merges with the sealing lip.

If the second connecting element is missing, the fastening element protrudes into the free cross section of the inner opening of the first connecting element. It is therefore advantageous, in accordance with a further embodiment of the invention, to provide a diametrical step between the annular groove in the connector and its sealing lip, in order to make it easier to intorduce the second connecting element into the connector attachment piece of the first connecting element.

The connection process is made even simpler if in accordance with a further characteristic of the invention the transition from the outer diameter of the connector to the diameter of the sealing lip is achieved by a conical oblique face, along which the fastening element is pressed slidingly into the unlocking position during the process of connecting the two connecting elements.

In the case of re-usable connectors, it is efficacious to provide the forward end of the connector, which is insertable into the connector attachment piece, with an annular groove in a diametrical step, an O ring seal being laid into this groove.

In the connection system according to the invention, Y pieces in which the connector is attached either in a straight line or at a right angle can be used. To advantageously provide such attachment especially for one-time use, it is advantageous for at least the first connecting element, for instance, the connector which is capable of being inserted into the receiving socket of the other connecting element and locked in place, to be made of plastic.

Naturally it is possible to fabricate the Y piece of plastic as well.

In a modified exemplary embodiment of the invention, the first connecting element is the connector attachment piece of a Y piece, and the other connecting element is the connector having the tube attachment. An annular groove is provided in the inner wall of the connector attachment piece while the at least one elastic fastening element is provided on the connector. For unlocking the at least one fastening element, at least one associated elastic unfastening element is provided, which passes through the jacket of the connector attachment piece in the vicinity of the annular groove.

In this exemplary embodiment, it is particularly advantageous that the at least one fastening element is formed as a locking tab either molded out of an annular wall of the connector, elastically protruding, or molded one or more ribs, while the at least one unfastening element is formed as a tab molded out of the wall of the connector attachment piece in the vicinity of the annular groove and protruding elastically therefrom. When the two connecting elements are in the locked state relative to one another, radial inward pressure on the unfastening tab forces the at least one elastically protruding or modled-on fastening element out of the annular groove and thus enables the axial disconnection of the connecting elements.

In a particularly advantageous manner, particularly for one-time use, a tube made of plastic (an endotracheal tube) is thermally welded to the connector.

In accordance with a further embodiment of the connection system, according to the invention, which is intended for respirator or anesthetic appliances. An artificial nose is provided which is releasably connected with one of the two connecting elements.

In accordance with a preferred exemplary embodiment, the first connecting element is a Y piece, the artificial nose is mountable on the Y piece as a cylindrical tube by means of a screw or bayonet mount, and its free end functions as a connector attachment.

It is thereby possible to dispose the artificial nose about the Y piece in connection with some arbitrary connector, or with a safety connector as well. In the embodiment of the connection as a screw or bayonet closure, a connector attachment piece can be threaded on while the Y piece remains unchanged, so that the unit can be connected with a corresponding connector.

In an efficacious manner, the screw or bayonet mount of the artificial nose has a lenticular ring seal disposed in a circular annular groove.

In an advantageous manner, a cylindrical, metal-coated plastic mesh screen is disposed within the artificial nose for the purpose of regulating the temperature and moisture content of the air for breathing. The plastic mesh screen is provided with a silver-nitrate coating. However, a nickel filter screen or the like can also be used in place of the plastic mesh screen.

One cylindrical section of sponge-like plastic foam is efficaciously disposed within the synthetic resin nose in the flow path of the breathing air before the air reaches the metal-coated plastic mesh screen, and another plastic foam section is disposed on the other side of the screen. These cylindrical sections of sponge-like plastic foam serve to regulate the moisture content of the fluid flowing past them, in particular that of the breathing air.

A particularly advantageous exemplary embodiment is characterized in that the plastic mesh screen and the plastic foam sections are combined in the form of a cartridge which can be interchangeably inserted into the plastic nose. As a result, the replacement of parts, required for regulating the temperature and moisture content of the fluid passing therethrough, can be effected in a simple manner, without having to remove the housing of the synthetic resin nose each time these parts have to be changed.

In order to further guarantee tightness of the seals in the connection system in respirator and anesthetic apparatuses, it is advantageous that the bifurcated pipes (inhalation hose connector end and exhalation hose connector end) of the one connecting element, which is embodied as a Y piece, are formed to be slightly conical, and each has at least one sawtooth-like annular bulge. The trailing edge of the sawtooth-like annular bulge is inclined more steeply than the leading edge, but it inclined at an angle of less than 90° relative to the longitudinal axis of the bifurcated pipe.

In addition, or as a modification, a further exemplary embodiment of the invention provides that the connecting element may be embodied as a Y piece and the breathing hose connector ends may be partially enveloped by flaps which are provided with partial circumferential slits at the throat of the Y piece. One axially displaceable, oval clamping ring passing all the way around the hose acts as a clamping means for each of the associated breathing hoses. As a result, a fixed and tight connection of the breathing hoses to the breathing hose connection ends of the Y piece is established, independently of the status of elasticity or of the aging of the breathing hoses to be fastened thereto.

In order to secure the axially displaceable, circular clamping ring on the Y piece such that it cannot be lost, it is advantageous for the flaps each to have a forward rim strip and the Y piece to have a rear rim strip in order to limit the axial displaceability of the clamping rings.

In a still further embodiment of the connection system according to the invention, bacteria filters known per se can be interchangeably disposed in the Y piece. They may be disposed in the vicinity of the breathing hose sockets, the connector attachment piece, or the artificial nose cartridge.

Further characteristics, details and advantages of the invention will be described below, referring to the drawings, which illustrate exemplary embodiments of the invention in a schematic fashion and without restricting the scope of the invention.

BRIEF DESCRIPTION OF THE DRAWINGS

FIG. 1 is a schematic perspective view of one exemplary embodiment of a connection system according to the invention;

FIG. 2a shows a Y piece and a connector, as the two connecting elements, in the unconnected position;

FIG. 2b shows a modification of a connector;

FIG. 2c shows a further modification of the connector;

FIG. 3a is a section taken through a Y piece along the line A—A of FIG. 2a;

FIG. 7b is a plan view on the Y piece looking in the direction of the arrow VII of FIG. 7a;

DESCRIPTION OF THE PREFERRED EMBODIMENTS

Figure 3A:
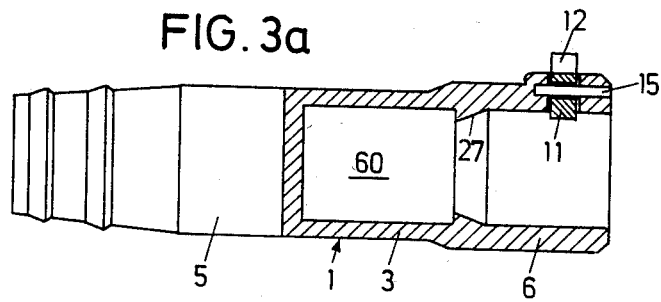

In FIG. 1, a connection system is shown in a schematic, perspective view and partially in section. The system comprises a bifurcated connecting element 1 in the form of a Y throat piece 3; a second connecting element 2 in the form of a connector 7 having a tube attachment 8, intended, for example, for an endotracheal tube. The Y piece includes an inhalation hose connector end 4 and exhalation hose connector end 5, disposed on the Y throat piece 3, with breathing hoses 53 being respectively connected with the inhalation hose connector end 4 and exhalation hose connector end 5 for connection with a respirator or anesthetic apparatus, for example. The Y throat piece 3 is attached to a connector attachment piece 6, into which the connector 7 can be inserted. A fastening element 11 is provided on the exterior surface of the connector attachment piece 6 and it includes an unfastening element 12. The design of the fastening element 11 and the unfastening element 12 and their cooperation with the second connecting element 2 will be discussed further in greater detail below.

Stringent demands are placed on the connection of the connecting elements 1 and 2, especially when they are used for breathing apparatus or the like, with particular importance being given to their being rotatable relative to one another, securely interconnected, and optionally disconnectable with one hand. Unintended disconnection should be prevented and completely tight seals should exist between the individual parts of the connection system, so that breathing air or the like cannot escape, and unintended changes in pressure in the system cannot occur. If there were leaks, then the fluid throughput (air for breathing, for instance, or anesthetic gas or the like) could be interrupted, causing problems with a patient's respiration and triggering alarm signals in monitoring apparatus attached to the connection system.

In FIG. 2a, the connection system is shown in section, in the disconnected state, and it is embodied by the connecting element 1 in the form of a Y throat piece 3 and the connecting element 2 in the form of a connector 7. A bacteria filter 14, known per se, may be interchangeably disposed within the Y throat piece 3.

In the exemplary embodiment of a connector 7 shown in FIG. 2a, an annular groove 10 is formed on the outer wall of the connector 7 and circumferentailly passes all the way around it. At the forward end area 13 of connecting element 2 which is introduceable into the Y throat piece 3 or the connector attachment piece 6, the connector 7 merges with a sealing lip 26 in conical fashion via a conical oblique face 30. An outer annular groove 28 is provided on the outer wall of the sealing lip 26 in order to enable elastic deformation of the sealing lip 26. In the inserted, locked state, the sealing lip 26 cooperates with an analogously shaped oblique wall section 27 in the connector attachment piece 6.

In the modified exemplary embodiment of the connector 7 as shown in FIG. 2b, a diametrical step 29 is provided between the annular groove 10 and the front oblique face 30 of the sealing lip 26, such that the fastening element 11 in the connector attachment piece 6, upon being unserted into the connector 7, is lifted out of its locking position and slid along the diametrical step 29 into its unlocked position. As the connector 7 is pushed further into the socket of connector attachment piece 6, the elastic fastening element then snaps securely into the annular groove 10.

The exemplary embodiments of the connector 7 according to FIGS. 2a and 2b are preferably intended for single-use connectors, which after a patient has been respirated are not re-used and are made of plastic in particular.

The exemplary embodiment according to FIG. 2c is intended for re-usable connectors 7, and a diametrical step 29 is provided; however, instead of the sealing lip 26, an O ring seal 32 is positioned within an annular groove 31.

As a result of the disposition of the sealing elements, that is, the sealing lip 26, or the O ring seal 32, on the surface of connector 7, sealing means in the inner opening of the connector attachment piece 6 are unnecessary. Thus, difficulty in attaching the sealing means is reduced and also the problem of sterilizing the sealing means after use is eliminated. There is furthermore no longer a danger that insufficient sealing may be attained between the connector element 1 and the connector element 2, that is, between the Y throat piece 3 and the connector 7 because the sealing element may have been forgotten or damaged. The absence in flaws of the sealing lip 26 and the presence of the O ring seal 32 can be checked before use in a simple manner.

In FIG. 3a, a section through a Y piece according to FIG. 1 or FIG. 2a is shown, taken along the plane of the arrows A—A of FIG. 2a.

The connector attachment piece 6, as shown, merges with the walls of two chambers 60, by means of which the connection to the breathing hose connector ends 4 and 5 of the Y piece is effected. The fastening element 11 is pivotably supported about a tongue 15 and is pressed by elastic spring action into the locking position shown in FIG. 3a. For unlocking, the fastening element 11 is lifted with the aid of the unfastening element 12, counter to the action of the spring, and lifted out the passageway opening of the inner opening in the connector attachment piece 6, so that a connector which has been introduced into the connector attachment piece 6 can be disconnected in a simple manner.

Figure 3B:
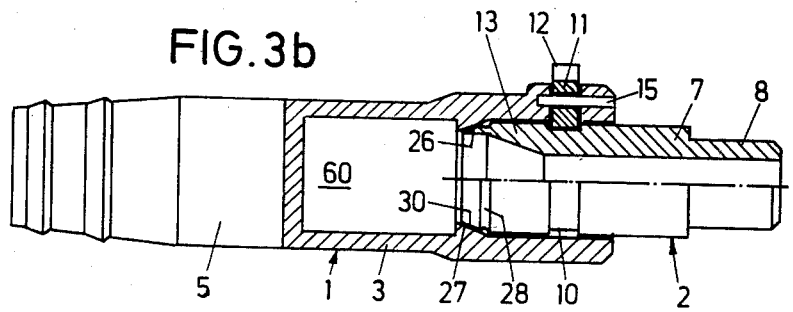
FIG. 3b is a view of the Y piece shown in FIG. 3a, with an inserted and locked connector.

FIG. 3b which is similar to FIG. 3a, shows a Y throat piece 3 with an inserted connector 7. The upper half of FIG. 3b shows a section through the connector 7 and the cooperation of the fastening element 11 with the annular groove 10. The lower half shows the connecting element 1, that is, the Y throat piece 3, in section and the connector 7, that is part of the connecting element 2, as seen from outside.

The function of the sealing lip 26 on the forward end of the connector 7 is shown in FIG. 3b. The sealing lip 26 rests with its conical oblique face 30 against a corresponding, analogously shaped conical wall section 27 of the inner opening of the connector attachment piece 6. By means of this embodiment, the sealing lip 26 is pressed against the inner wall of the Y throat piece 3 or against connector attachment piece 6 and firmly sealed thereagainst by the internal pressure in the connecting line system.

Figure 4A:
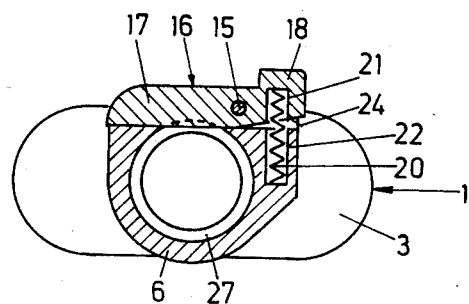
FIG. 4a shows an exemplary embodiment of a Y piece having a connector mounted in straight-line fashion.

In FIG. 4a, the Y throat piece 3 is shown in an end view of the connector attachment piece 6. It may be seen that the fastening element 11 is embodied as a two-armed lever 16, with an inner lever arm 17 and an outer lever arm 18. The inner lever arm 17 forms the fastenting element 11, which engages the annular groove 10 of the connector 7 and locks the connection assembly. The two-armed lever 16 is pivotable about the tongue 15. A spring element, for instance a spiral cylindrical spring 20 or the like, is supported in an inner bore 22 in the connector attachment piece 6 and in the illustration of FIG. 4a, presses the lever 16 in the counterclockwise direction, with the inner lever arm 17 being disposed downward. The outer lever arm 18 has an oblique face 24, which on the one hand enables the tilting of the lever 16 about the tongue 15 within a predetermined angular range and on the other hand limits the stroke movement of the fastening element 11, that is, of the lever arm 17.

Figure 4B:
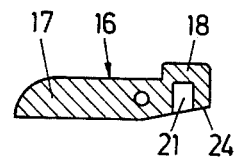
FIG. 4b is a detail of a fastening element.

In FIG. 4b, the fastening element 11 is shown separately, in the form of the lever 16.

Figure 4C:
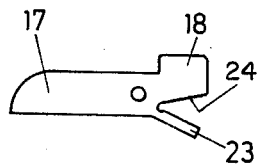
FIG. 4c shows a modified exemplary embodiment of a fastening element.

FIG. 4c shows a modification of a fastening element 11, in the form of a two-armed lever 16 having an inner lever arm 17 and an outer lever arm 18 of plastic, with a yielding rib 23 molded on the outer lever arm 18 to act as a spring element. The yielding rib 23, because of its elasticity, takes over the function of the spring element such as the helical spring 20. An oblique face, corresponding to the oblique face 24 in the exemplary embodiment shown in FIG. 4a or FIG. 4b, must be provided on the connector attachment piece 6 in this exemplary embodiment as well.

Figure 5:
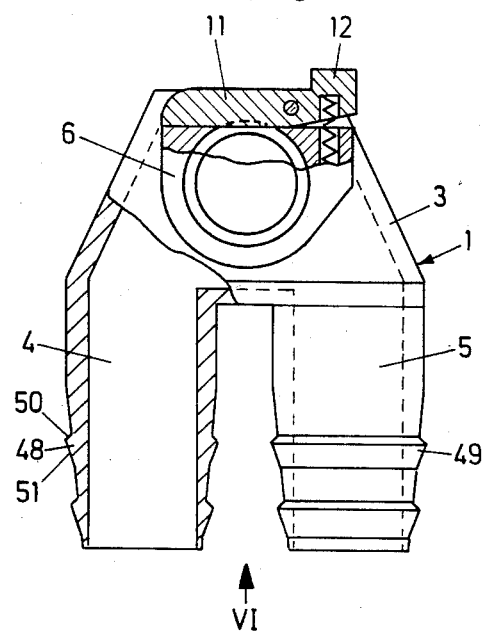
FIG. 5 shows, partially in section a modified Y piece having a connector mounted perpendicularly.
Figure 6:
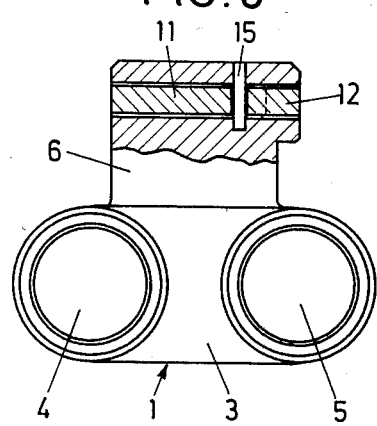
FIG. 6 shows a partial section of the exemplary embodiment of FIG. 5, seen in the direction of the arrow VI.

In the exemplary embodiments of FIGS. 1–4, a Y throat piece 3 is shown onto which the connector attachment piece 6 has been attached in a straight line. In FIGS. 5 and 6, a modified exemplary embodiment is shown in which the connector attachment piece 6, and thus the connector 7 as well, are mounted at right angles on the Y throat piece 3.

The fastening element 11 and the unfastening element 12 are identical in structure to those shown in FIGS. 4a–4c.

As further means of securely fastening the connection system assembly, at least one sawtooth-like annular bulge 48 or 49, respectively, is molded onto the connecting element 1 of FIG. 5, that is, onto the Y throat piece 3 and specifically onto each of the breathing hose connector ends (bifurcated pipe) 4 and 5. These bulges 48 and 49 serve to effect better adherence of the breathing hoses (not shown). By means of this embodiment, proper account is taken of the fact that after repeated use and disinfection or sterilization, the breathing hoses, if made for instance of rubber or plastic with inlaid reinforcements, age and lose their elasticity. The sawtooth-like annular bulges 48 and 49 assure that each time the breathing hoses are connected with the breathing hose connector ends 4, 5, they will be firmly seated. The embodiment is designed such that the trailing edge 50 of the sawtooth-like annular bulges 48 and 49 is inclined more steeply than the leading edge 51, but is still inclined at an angle of less than 90° relative to the longitudinal axis of the bifurcated pipe (that is, the connector ends 4 and 5).

FIG. 6 shows a Y throat piece 3 with a connector attachment piece 6 mounted at a right angle, partially in section and viewed in the direction of the arrow VI of FIG. 5.

Figure 7A:
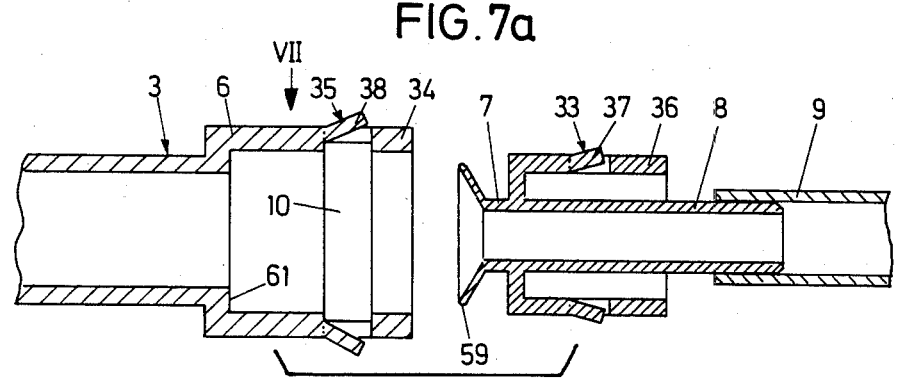
FIG. 7a shows a modified exemplary embodiment of the Y piece and of the connector in sectional form.

In FIG. 7a, a connection system comprising a Y throat piece 3 and a connector 7 is shown in modified form. In this exemplary embodiment, at least one fastening element 33 is provided on the connector 7, while the annular groove 10 is disposed in the inner wall or jacket 34 of the connector attachment piece 6 of the Y throat piece 3. The at least one fastening element 33 of the connector 7 is preferably disposed on an additional annular wall 36. Instead of a complete annular wall, one rib (or more) can be provided, on which the fastening element 33 is molded. An endotracheal tube 9 is again mounted, by way of example, on the tube attachment 8.

The exemplary embodiment of FIG. 7a is particularly well suited to being made of plastic, with the at least one fastening element 33 being molded out of the annular wall 36 in the form of a locking tab 37 and protruding elastically outward therefrom, or being molded onto one (or more) ribs. Upon the insertion of the connector 7 into the connector attachment piece 6, the locking tab 37 then, because of its elasticity, comes to rest inside the annular groove 10 and thus prevents the unintentional disconnection of the two connecting elements.

For the purpose of intentional disconnection, at least one unfastening element 35 is provided in the jacket or wall 34 of the connector attachment piece 6. This unfastening element 35 includes an unlocking tab 38 protruding elastically outward, which can be selectively pressed into the vicinity of the annular groove 10 counter to its own elastic spring force. As soon as the fastening element 33 and the unfastening element 35, or the connector 7 and connector attachment piece 6, are in a specific, definite position relative to one another then, by means of pressure exerted on the unfastening element 35, the fastening element 33 can be pressed in so that it is in alignment with the surface of the annular wall 36; thus the fastening element 33 will leave the annular groove 10, and the connector 7 can be removed (toward the right as seen in the drawing) from the Y throat piece 3.

In this exemplary embodiment, a sealing means is embodied in the form of a conical sealing cone 59. When the connector 7 is connected with the Y throat piece 3, the sealing cone 59 comes to rest in an elastically yielding manner against an end wall 61 in the Y throat piece 3. A sealing means, in the form of a circular ring for instance, may be disposed inside the connector attachment piece 6 in this exemplary embodiment, with the sealing cone 59 resting against this sealing means.

Figure 7B:
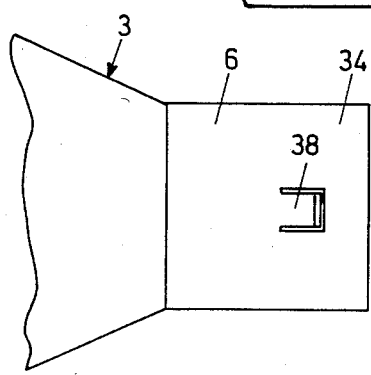

FIG. 7b is a plan view of the connector attachment piece 6 of FIG. 7a, seen in the direction of the arrow VII. As shown by the drawing, the at least one unlocking tab 38 is molded out of the wall 34. It is not necessary for the locking tab 37 and the unlocking tab 38 to be rectangular; they may, for example, also be semicircular in shape.

Figure 8:
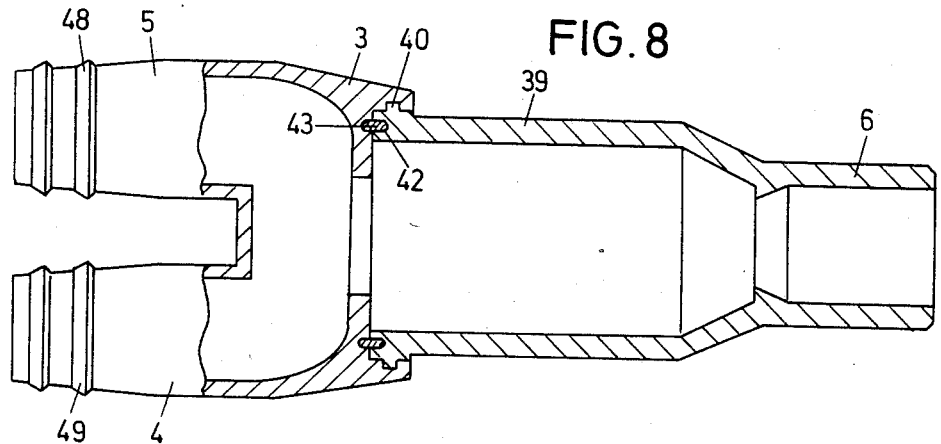
FIG. 8 shows a Y piece with an attachment piece for a synthetic resin nose.
Figure 9:
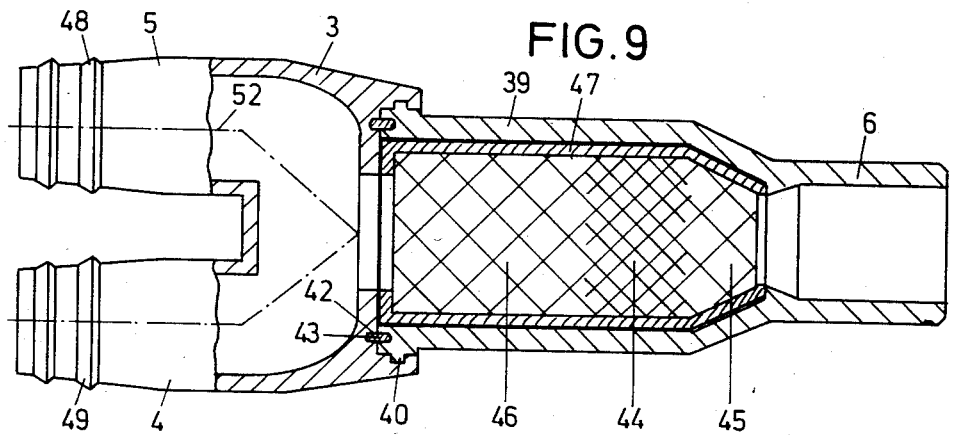
FIG. 9 shows the exemplary embodiment of FIG. 8 with a synthetic resin nose provided with an insertable cartridge.

In FIGS. 8 and 9, a further-modified exemplary embodiment is shown, having a Y throat piece 3 which is connectable with a synthetic resin nose 39 by means of a screw or bayonet closure 40. A lenticular ring seal 43 is disposed in an annular groove 42. The synthetic resin nose 39 is attached to the required connector attachment piece 6, which is located on its end remote from the Y throat piece 3. The connector attachment piece 6 may be embodied in a manner corresponding to the exemplary embodiments described above and shown in FIGS. 1–7.

As is well known, artificial noses in respirator apparatuses serve to influence the moisture content and temperature of the breathing air, in order to compensate for the lack of influence of the nasal-pharyngeal cavity, of the patient being respirated on the status of the air being breathed.

In FIG. 9, an exemplary embodiment of an artificial nose is shown in which a cartridge 47 is introduced into the artificial nose 39; a metal-coated plastic mesh screen 44, embodied in cylindrical form by way of example, is provided inside this cartridge 47. Silver nitrate is particularly suitable as a coating. However, a nickel filter screen or a similarly functioning element may also be inserted in place of the plastic mesh screen. One cylindrical plastic foam section 45 and 46, respectively, is disposed before and after the plastic mesh screen 44 in the flow path of the breathing air, the plastic foam serving to regulate the moisture content by absorption of the moisture in the breathing air which flows past the foam sections.

The artificial nose 39 with a cartridge 47 may be used in combination with conventional connectors; on the other hand, with Y throat piece 3 embodied in accordance with FIGS. 8 and 9, connector attachment pieces 6 can be connected directly with the Y throat piece 3 by means of the screw or bayonet closure 40 without interposing an artificial nose 39 between them.

Figure 10:
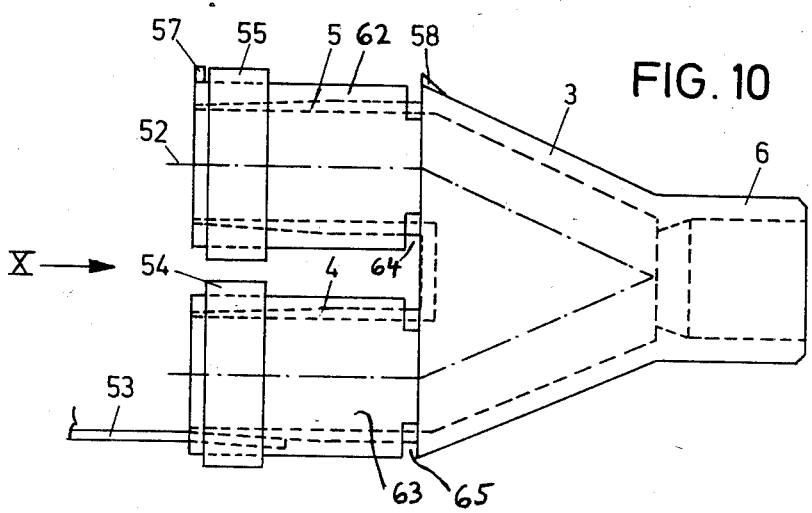
FIG. 10 shows a modified exemplary embodiment of a Y piece having slotted flaps and fastened breathing hose connector ends.

In FIG. 10, a modified exemplary embodiment of a fastening means for breathing hoses 53 connected to the breathing hose connector ends 4, 5 is shown. Here, flaps 62, 63 are provided which partially envelop the respective breathing hose connector ends 4 and 5; this is accomplished in a particularly simple fashion when the Y throat piece 3 is made of plastic. Each of the flaps 62, 63 carries an oval clamping ring 54 and 55, respectively, which are displaceable parallel to the longitudinal socket axis 52. The oval embodiment is advantageous particularly because, given the restricted space between the breathing hose connector ends 4 and 5, the disposition of a round clampling ring would mean that increased space would be required.

Figure 11:
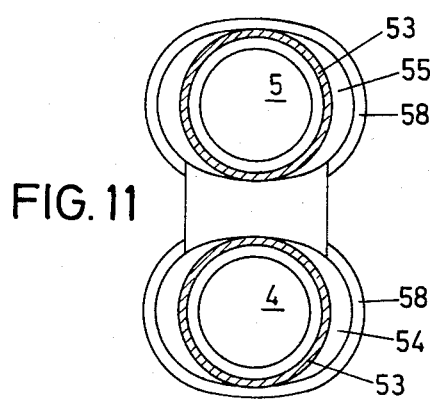
FIG. 11 is a view of the exemplary embodiment of FIG. 10, seen in the direction of the arrow x.

In order to prevent unintended loosening of the clamping rings 54 and 55, it is advantageous for a forward rim strip 57 to be disposed on the flaps 62, 63 and a rear rim strip 58 to be disposed on the Y throat piece 3. The oval clamping rings 54 and 55 can be mounted or removed, if no breathing hose has been inserted, by means of elastic deformation of the slotted breathing hose connector ends 4 and 5. FIG. 11 shows a Y throat piece 3 like that of FIG. 10, here seen in the direction of the arrow X of FIG. 10.

Figure 12:
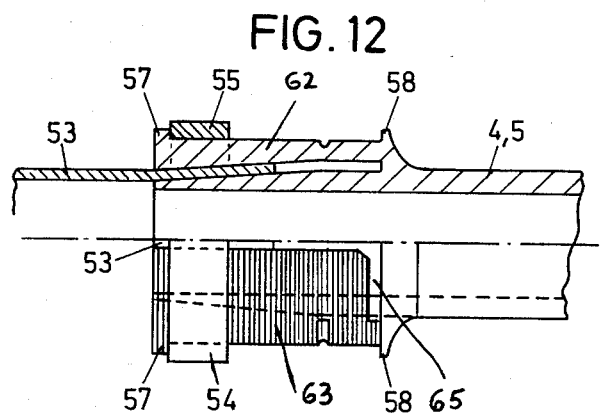
FIG. 12, at the top, is a section through an exemplary embodiment as in FIG. 10 and, at the bottom, is a plan view of a flap having a clamping ring.

Finally, FIG. 12 shows the fastening system of the exemplary embodiment of FIGS. 10 and 11, in combination with an inserted or mounted breathing hose 53; in the upper part of the drawing, the system is shown in sectional form, and in the lower part of the drawing it is seen from the side.

The connecting elements 1 and 2, for instance the Y throat piece 3 and connector 7, may be fabricated either of metal of of plastic, the latter being particularly suitable for one-time use, in all the described embodiments of the invention. It is also possible to use a metal/plastic combination; for instance, the Y piece may be fabricated of metal, and the connector 7 may be of plastic. In the case of plastic, it is possible in an advantageous manner to weld the tube (endotracheal tube) 9 to the tube attachment 8 of the connector 7, for instance by the suitable application of heat to a thermoplastic synthetic material. Welding the tube 9 to the connector 7 eliminates yet another releasable connecting point which could have been the source of an unintended disconnection of the system. Fabricating the connector 7 and endotracheal tube 9 in one piece (that is, welded) additionally makes possible greater ease of manipulation and a reduction in bearing support means.

The connection/fastening system according to the invention is intended for connecting elements 1 and 2 which are disposed in the path of a fluid line, which may also carry compressed air or water or, with an appropriate selection of the plastic material or of metal, oils or hydraulic oils whenever a secure connection and a simple means of intentional disconnection within seconds are required for such fluid lines.

The invention is not restricted to the exemplary embodiments shown and described herein. It also encompasses all modifications and further embodiments within the competence of one skilled in the art, as well as partial and subsidiary combinations of the characteristics and provisions shown and/or described.

What is claimed is:

1. A connection system for respirator or anesthesia units with a Y-piece including an inhalation hose socket, an exhalation hose socket and a connector attachment piece, as well as a tubular connector having two open ends, one end portion thereof capable of being inserted into the connector attachment piece and having a tube attachment at the opposite end portion adapted to receive an endotracheal tube thereon, and further including said connection system having one connecting element having a first annular groove disposed in its outer circumference, and said connection system having another connecting element including at least one spring-biased fastening means disposed thereon for elastically engaging the annular groove under spring action, the connecting elements being freely rotatable relative to one another, said connection system comprising:

at least one selectively actuable hand-operable unfastening means for temporarily overriding the spring action of said at least one fastening means, sealing means disposed on said one connecting element and cooperating with the inner circumference of said other connecting element, said other connecting element constituting the connector attachment piece of said Y-piece and the one connecting element constituting the one end portion of said connector with the tube attachment, said at least one spring-biased fastening means being provided on said connector attachment piece transversely to its longitudinal axis, said at least one spring-biased fastening means comprising a lever having inner and outer arms, a pivot and means for spring-loading the outer arm, said connector attachment piece including a slot extending through the sidewall thereof transverse to its longitudinal axis and sized to receive the lever therein, said lever positioned in said slot such that at least a portion of the inner lever arm thereof extends into the lumen of the connector attachment piece and said pivot extending through said slot and said lever parallel to the longitudinal axis of the connector attachment piece whereby one of said arms is movable relative to the other in a plane transverse to the longitudinal axis of said connector attachment piece, said spring loading means including a spring element engaging the connector attachment piece at one end and the outer arm at the other, said spring element biasing the inner arm of said lever into engagement with the annular groove.

2. A connection system as defined by claim 1, wherein both the portion of the outer lever arm engaging said spring means and the portion of said connector attachment piece engaging said spring element include an inner bore, and said spring element comprises a spiral helical spring, the ends of which are disposed in the inner bores, of the outer lever arm and the connector attachment piece, respectively.

3. A connection system as defined by claim 1 wherein said spring element comprises a yielding rib means having opposite first and second ends, one end thereof mounted on said outer lever arm and engaging the connector attachment piece at the second end thereof, said rib means being biased away from said outer lever arm to bias the inner lever arm in engagement with the connector attachment piece.

4. A connection system as defined by claim 3, wherein the surface of said outer lever arm covered by said yielding rib means has an oblique face which defines, with the connector attachment piece, said means for unfastening the fastening element, and defines means for limiting the range of pivotal movement of the outer lever arm during the unlocking stroke thereof.

5. A connection system as defined by any one of claims 1, 2, 3, or 4 wherein the lumen of the connector which is insertable into the connector attachment piece comprises a first portion of substantially constant diameter remote from the open end of said one end portion and a second portion extending from said first lumen portion to the open end of said one end portion, the diameter of said second portion gradually increasing along its length from that of the first portion to the outer diameter of the open end of said one end portion and said sealing means includes a sealing lip defined by the peripheral edge of the open end of said one end portion, and groove means disposed adjacent said sealing lip for enabling elastic deformation of said sealing lip, the lumen wall of the connector attachment piece being shaped complementary to said one end portion of the tubular connector, and means for cooperatively engaging said sealing lip being provided within the lumen of said connector attachment piece whereby when said one end portion is inserted into said connector attachment piece, said lip elastically engages said engagement means and the mutual locking between the groove and the fastening element of the two connecting elements effects a contacting pressure between said sealing lip and said engaging means to define a seal therebetween.

6. A connection system as defined by claim 5, wherein an outer annular diametrical step is provided about said one end portion between said first annular groove in the connector and said groove means.

7. A connection system as defined by claim 6, wherein said fastening element is slidingly pressed by said diametrical step into the unlocking position in the course of the connection process of the two connecting elements.

8. A connection system as defined by any one of the claims 1, 2, 3 or 4, wherein the first annular groove is disposed remote from the open end of said one end portion, the one end portion of the connector, which is insertable into the connector attachment piece, further includes an outer annular diametrical step disposed between the open end thereof and said first groove, said sealing means including a second outer annular groove disposed adjacent the open end of said one end portion and an O ring seal inlaid in the groove.

9. A connection system as defined by any one of the claims 1, 2, 3 or 4, wherein at least said tubular connector which is insertable into the other connecting element and lockable is fabricated of plastic.

10. A connection system as defined by claim 1, for respirators or anesthetic units wherein the exhalation hose socket and the inhalation hose socket of the Y-piece connected to the connector attachment piece are shaped to be slightly conical in the top plane view and each has at least one sawtooth-shaped annular ring and the one edge of the sawtooth-shaped ring adjacent said connector attachment piece is inclined more steeply than the other edge remote from said connector attachment piece but less than an angle of 90° relative to the longitudinal axis of the hose sockets.

11. A connection system as defined by claim 1, for respirators or anesthetic units, wherein bacteria filters are removably disposed in the Y-piece.

* * * * *